United States Patent [19]

Phillion

[11] Patent Number: 4,740,608

[45] Date of Patent: Apr. 26, 1988

[54] (PHOSPHONOMETHYL)TRI-FLUOROMETHYL SULFONATES

[75] Inventor: Dennis P. Phillion, St. Charles, Mo.

[73] Assignee: Monsanto Company, St. Louis, Mo.

[21] Appl. No.: 785,942

[22] Filed: Oct. 9, 1985

[51] Int. Cl.[4] ............................................. C07C 143/68
[52] U.S. Cl. ................... 558/45; 260/502.5 F; 558/87
[58] Field of Search .................. 260/456 R, 456 F; 558/45

[56] References Cited

U.S. PATENT DOCUMENTS

| | | | |
|---|---|---|---|
| 3,927,080 | 12/1975 | Gaertner | 260/502.5 F |
| 3,969,398 | 7/1976 | Hershman | 260/502.5 |
| 4,237,065 | 12/1980 | Ehrat | 260/502.5 |
| 4,670,554 | 6/1987 | Koster et al. | 540/355 |

FOREIGN PATENT DOCUMENTS 127177 12/1984 European Pat. Off. .

OTHER PUBLICATIONS

Creary, et al, "Stabilization Demands of Diethyl Phosphonate Substituted Carbocations as Revealed by Substituent Effects", *J. Org. Chem.* 50, 1985, pp. 2165–2170.

*Primary Examiner*—Nicky Chan
*Attorney, Agent, or Firm*—Frank D. Shearin

[57] ABSTRACT

The compound (phosphonomethyl)perfluoroalkyl sulfonate can be represented by the formula

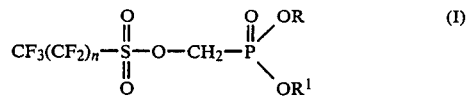

(I)

wherein n is from 0 to 7 and R and R[1] are independently selected from the group consisting of hydrogen, 2-cyanoethyl, monovalent hydrocarbons containing from 1 to 18 carbons, monovalent hydrocarbonoxyhydrocarbons containing from 1 to 18 carbons, halogenated monovalent hydrocarbons containing from 1 to 18 carbons and from 1 to 3 halogens, halogenated monovalent hydrocarbonoxyhydrocarbons containing from 1 to 18 carbons and from 1 to 3 halogens. The compound is useful as an intermediate to prepare amino-phosphorous compounds such as N-phosphonomethylglycine.

8 Claims, No Drawings

(PHOSPHONOMETHYL)TRIFLUOROMETHYL SULFONATES

BACKGROUND OF THE INVENTION

This invention relates to novel intermediates useful for the preparation of the well-known herbicide N-phosphonomethylglycine, and more particularly relates to the novel compounds (phosphonomethyl)perfluoroalkyl sulfonates.

N-phosphonomethylglycine, known in the agricultural chemical art as glyphosate, is a highly effective and commercially important phytotoxicant useful in controlling the growth of germinating seeds, emerging seedlings, maturing and established woody and herbaceous vegetation and aquatic plants. Glyphosate and its salts are conveniently applied in an aqueous formulation as a post-emergent phytotoxicant, or herbicide, for the control of one or more annual or perennial weed species. Such compounds are characterized by broad spectrum activity, i.e., they control the growth of a wide variety of plants.

Hershman, U.S. Pat. No. 3,969,398, describes a process for preparing glyphosate in which iminodiacetic acid is reacted with formaldehyde and phosphorous acid to produce N-phosphonomethyliminodiacetic acid as an intermediate, which is then oxidized to produce glyphosate.

Gaertner, U.S. Pat. No. 3,927,080, describes the production of glyphosate by the acid hydrolysis of N-t-butyl-N-phosphonomethylglycine or its esters. Tertiary butylamine is reacted with a bromoacetate ester to produce an ester of N-t-butylglycine which is in turn reacted with formaldehyde and phosphorous acid to produce the N-t-butyl-N-phosphonomethylglycine precursor.

Ehrat, U.S. Pat. No. 4,237,065, describes a process in which N-phosphonomethylglycine is prepared starting from glycine, formaldehyde and a tertiary base in an alcoholic solution. After completion of the reaction, a dialkylphosphite is added and the reaction product is hydrolyzed and then acidified to precipitate the product.

Creary et al, in *J. Org. Chem.*, 50, 1985, pp. 2165–2170, discloses the triflate derivative of diethyl-(1-hydroxyethyl)phosphonate, but does not disclose any use for such compounds. Although such compounds are within the same general class of chemistry as the ones described herein, the structures are far different, and again no utility is disclosed.

Although satisfactory processes for the preparation of N-phosphonomethylglycine are disclosed in the above references and other references in the prior art, there is a need for yet other processes to prepare N-phosphonomethylglycine, especially processes that provide such a product in high yields and under mild reaction conditions. In addition, the compounds of this invention can also be used to prepare other amino-phosphorus compounds.

SUMMARY OF THE INVENTION

These and other differences and advantages not disclosed in the prior art are achieved by the use of an intermediate compound for the preparation of N-phosphonomethylglycine, the compound represented by the formula:

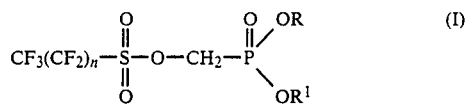

wherein n is from 0 to 7, and R and $R^1$ are independently selected from the group consisting of hydrogen, 2-cyanoethyl, monovalent hydrocarbons containing from 1 to 18 carbons, monovalent hydrocarboxyhydrocarbons containing from 1 to 18 carbons, halogenated monovalent hydrocarbons containing from 1 to 18 carbons and from 1 to 3 halogens, and halogenated monovalent hydrocarbonoxy hydrocarbons containing from 1 to 18 carbons and from 1 to 3 halogens.

DETAILED DESCRIPTION OF THE INVENTION

The compounds of the present invention can be prepared by the sulfonylation of an hydroxymethyl phosphonate. Common procedures include reacting the hydroxymethyl phosphonate with trifluoromethyl sulfonic anhydride and a pyridine base in a halogenated solvent or reacting its corresponding sodium alkoxide with trifluoromethanesulfonyl chloride in ethereal solvents. The phosphonylmethylperfluoroalkyl sulfonates of the present invention can also be prepared by the addition of trifluoromethane sulfonic acid to an alpha-diazophosphonate. Other (phosphonomethyl)perfluoroalkyl sulfonates can be prepared using similar procedures. These materials are lipophilic oils or solids which are quite stable when stored at below ambient temperatures and are generally stable to chromatographic purification procedures on silica gel. Such procedures provide compounds which can be represented by the formula

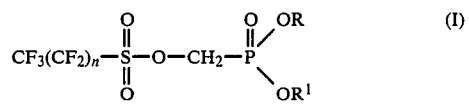

wherein n is from 0 to 7 and R and $R^1$ are independently selected from the group consisting of hydrogen, 2-cyanoethyl, or monovalent hydrocarbons containing from 1 to 18 carbons, monovalent hydrocarbonoxyhydrocarbons containing 1 to 18 carbons, halogenated monovalent hydrocarbons containing from 1 to 18 carbons and 1 to 3 halogens, and halogenated monovalent hydrocarbonoxyhydrocarbons containing from 1 to 18 carbons and from 1 to 3 halogens.

In the above formula, n can vary from 0 to 7; however, for the purposes of preparing N-phosphonomethylglycine there does not seem to be a particular advantage to having excess fluorocarbon present and for that purpose it is preferred that n equals 0. However, for the preparation of other compounds, it may be desirable that n vary between 0 and 7.

As noted above, R and $R^1$ are independently selected from the group consisting of hydrogen, 2-cyanoethyl, monovalent hydrocarbons, monovalent hydrocarboxyhydrocarbons, halogenated monovalent hydrocarbons and halogenated monovalent hydrocarbonoxyhydrocarbons. It is preferred that R and $R^1$ are independently selected from the group consisting of hydrogen, 2-cyanoethyl and monovalent hydrocarbon groups containing less than 9 carbon atoms.

The term halogen as employed herein means chlorine, bromine, iodine and fluorine.

The term monovalent hydrocarbon as used herein includes alkyl, alkenyl, alkynyl, aralkyl inclusive of both straight and branched chain radicals, such as methyl, ethyl, isopropyl, cyclopropyl, cyclohexyl, tertiary butyl, n-butyl and the various forms of amyl, hexyl, heptyl, octyl, nonyl, decyl, undecyl, dodecyl, tridecyl, tetradecyl, pentadecyl, hexadecyl, heptadecyl, octadecyl, benzyl, phenylethyl, naphthylethyl, tolylethyl, methylbenzyl, phenylbenzyl, and the corresponding alkenyl and alkynyl groups and the like, aryl groups and alkaryl groups such as phenyl, tolyl, xylyl, naphthyl, vinylphenyl and the like. It is preferred that such monovalent hydrocarbons contain from 1 to 18 carbons and be alkyl, aryl, or aralkyl groups.

The term monovalent hydrocarbonoxyhydrocarbon include alkoxyalkyl, alkenoxyalkyl, alkoxyalkoxyalkyl, alkenoxyalkoxyalkyl, dialkoxyalkyl, alkenoxy (alkoxy) alkyl, alkenoxyalkoxy(alkoxy)alkyl, alkoxyalkoxy(alkoxy)alkyl, aryloxyalkyl and alkoxyaryl such as 2-methoxyethyl, 4-ethoxy-2-methylbutyl, 2-ethoxyethyl, 3-propoxypropyl, 4-methoxybutyl, 4-methoxy-2-ethylbutyl, 4-butoxybutyl, 2-allyloxyethyl, 2-butenoxyethyl, 4-butenoxybutyl, 2-(2-methoxyethoxy)ethyl, 2-(2-butoxyethoxy)ethyl, 4-(3-methoxypropoxy)butyl, 2-(3-allyloxypropoxy)ethyl, 2-(2-butenoxyethoxy)ethyl, phenoxyethyl, naphthoxyethyl, 2,4-diethoxyphenol, 2-methoxyphenyl, tolyloxyethyl, 4-phenoxybutyl, trifluoromethylphenyl, and the like.

Illustrative of the halogenated monovalent hydrocarbon groups are haloalkyl such as chloroethyl, iodoethyl, bromoethyl, 2,2-dibromoethyl, chloro-n-propyl, bromo-n-propyl, iodoisopropyl, bromo-n-butyl, bromo-tert-butyl, chloropentyl, bromopentyl, 2,3-dichloropentyl, 3,3-dibromopentyl, chlorohexyl, bromohexyl, 2,4-dichlorohexyl, chloroheptyl, bromoheptyl, fluoroheptyl, 2,4-dichloromethylheptyl, chlorooctyl, bromooctyl, iodooctyl, 2,4-dichloromethylhexyl, 2,4-dichlorooctyl, 2,4,4-trichloromethylpentyl and the halogenated straight and branched chain nonyl, decyl, undecyl, dodecyl, tridecyl, tetradecyl, pentadecyl, hexadecyl, heptadecyl and octadecyl; haloalkenyl such as chlorovinyl, bromovinyl, chloroallyl, bromoallyl, 3-chloro-n-butenyl-1, 3-chloro-n-pentenyl-1, 4-chloro-n-hexenyl-2, 3,4-dichloromethylpentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologues and isomers of haloalkenyl having 2 to 12 carbon atoms; haloaryl such as o-chlorophenyl, m-chlorophenyl, m-bromophenyl, p-chlorophenyl, 2,4-dichlorophenyl, 3,5-dichlorophenyl, 2,5-diiodophenyl, and the like. The halogenated monovalent hydrocarbonoxyhydrocarbons are the alkoxy and aryloxy substituted derivatives of the foregoing halogenated monovalent hydrocarbon groups where the alkyl and aryl groups are those previously set forth.

The (phosphonomethyl)perfluoroalkyl sulfonates undergo mild displacement of the perfluoroalkyl sulfonate-leaving group, thus providing a mild and general method for effecting displacement reactions on the alpha carbon of the phosphonate. The compounds of the present invention undergo displacement reactions with various nitrogen, sulphur, oxygen, phosphorous, carbon and halogen nucleophiles rapidly, under mild reaction conditions, and in good yield.

The (phosphonomethyl)perfluoroalkyl sulfonates of the present invention can be reacted with nucleophiles in anhydrous solvents such as toluene, methylene chloride, diethyl ether and the like, in the presence of a proton acceptor. Water-soluble amines can also be reacted with the (phosphonomethyl)perfluoroalkyl sulfonates under Schotten-Baumann conditions in the presence of a proton acceptor, such as sodium hydroxide or sodium carbonate.

The displacement reactions can be conducted from at least −78° C. to at least 40° C. and the reaction can be monitored to completion with ease using $^{31}$P-NMR spectroscopy.

Using the compounds of this invention N-phosphonomethyl glycine can be readily prepared by bringing together under reaction conditions the (phosphonomethyl)perfluoroalkyl sulfonate and the sodium salt of glycine to provide an ester of N-phosphonomethylglycine, and thereafter, converting the precursor to N-phosphonomethylglycine by contacting the precursor with a strong mineral acid such as hydrochloric acid or hydrobromic acid.

The invention is further illustrated by, but not limited to, the following examples:

EXAMPLE 1

Diethyl(phosphonomethyl)perfluoromethyl Sulfonate

Trifluoromethanesulfonyl chloride (38.06 ml, 356 mmol) was added in a single portion to a −20° C. cooled mixture of 99% granular sodium hydride (9.28 g, 386 mmol) in diethyl ether (500 ml), and was followed immediately by the rapid dropwise addition of a solution of diethyl hydroxymethylphosphonate (50.0 g, 297 mmol) in diethyl ether (100 ml), maintaining an internal reaction temperature between −20° C. and −15° C. After the reaction mixture was stirred one hour at −20° C., hydrogen evolution had almost ceased so the mixture was rapidly filtered through celite to remove the remaining sodium hydride, then was diluted with methylene chloride (1000 ml) and thoroughly extracted three times with saturated aqueous sodium bicarbonate (3×35 ml). The organic solution was dried over magnesium sulfate and concentrated to afford 71.36 g (80%) of diethyl(phosphonomethyl)perfluoromethyl sulfonate as a colorless oil.

For $C_6H_{12}F_3O_6PS$:

|  | C | H | F | P | S |
|---|---|---|---|---|---|
| Calcd: | 24.01; | 4.03; | 18.99; | 10.32; | 10.68 |
| Found: | 23.74; | 4.04; | 18.72; | 10.44; | 10.53. |

EXAMPLE 2

(Phosphonomethyl)perfluoromethyl Sulfonate

The compound N,O-Bis(trimethylsilyl)acetamide (20.6 ml, 83.3 mmol) was syringed into an ice-water cooled mixture of di-tert-butylphosphite (14.78 g, 75.6 mmol) and triethylamine (0.5 ml, 3.6 mmol). After 20 minutes the reaction mixture was warmed to room temperature and stirred overnight. The $^{31}$P-NMR showed the reaction to be complete with a single peak at 131 ppm. Methylene chloride (150 ml), then paraformaldehyde (11.41 g, 380.5 mmol) was added. This suspension was stirred overnight at room temperature, and the $^{31}$P-NMR again showed complete reaction with a single peak at 15 ppm. The excess paraformaldehyde was removed by filtration through celite, then the filtrate was extracted with a small volume of water. Concentration of the organic solution gave crude silyl ether which was desilylated with water (25 ml) plus enough acetonitrile to effect solution. The progress of desilylation was conveniently monitored by $^{31}$P-NMR to afford di-tert-butyl hydroxymethylphosphonate with a chemical shift of 17.1 ppm. Most of the acetonitrile was then removed under vacuum, and the concentrate partitioned between methylene chloride and water. The aqueous phase was back-extracted with methylene chloride, then the combined organic solutions were dried over magnesium sulfate, concentrated and chromatographed (silica gel eluted with 1:9 cyclohexane/ethyl acetate) to afford 13.0 g (76%) of di-tert-butyl hydroxymethylphosphonate as a white solid (mp 100°–101.5° C.).

For $C_9H_{21}O_4P$:

|  | C | H | P |
| --- | --- | --- | --- |
| Calcd: | 48.21; | 9.44; | 13.81 |
| Found: | 48.27; | 9.51; | 14.04. |

A solution of di-tert-butyl hydroxymethylphosphonate (8.9 g, 39.5 mmol) in tetrahydrofuran (45 ml) was added dropwise to a mixture of sodium hydride (1.42 g, 59 mmol) in tetrahydrofuran (100 ml). Gas evolution proceeded at a slow rate so the reaction mixture was stirred overnight at room temperature. The resulting slurry of alkoxide was added dropwise to a dry ice/acetone cooled, mechanically stirred solution of trifluoromethanesulfonyl chloride (12.6 ml, 118 mmol) in tetrahydrofuran (80 ml), maintaining an internal reaction temperature less than −65° C. The resulting mixture was stirred an additional 20 minutes at −78° C., then was warmed to −20° C., filtered, and concentrated under vacuum to an oil. This material was dissolved in methylene chloride and extracted with small portions of saturated aqueous sodium bicarbonate, then was dried over magnesium sulfate, and concentrated under vacuum to afford 13.3 g (94%) of di-tert-butyl(phosphonomethyl)perfluoromethyl sulfonate as an oil. This material exhibited a single peak in the $^{31}$P-NMR spectrum at 4.1 ppm and was stable for at least one day when stored in the refrigerator, but on standing at room temperature, isobutylene gas was rapidly evolved to afford a quantitative yield of pure (phosphonomethyl)perfluoromethyl sulfonate as a white solid.

EXAMPLE 3

Diphenyl(phosphonomethyl)perfluoromethyl Sulfonate

A solution of iodotrimethylsilane (14.34 ml, 101 mmol) in methylene chloride (20 ml) was rapidly added dropwise to an ice-water cooled mixture of paraformaldehyde (3.02 g, 101 mmol) in methylene chloride (40 ml). Within a few minutes all of the paraformaldehyde dissolved. Then, a solution of methyl diphenylphosphite (25.0 g, 101 mmol) in methylene chloride (40 ml) was added dropwise. The first few drops of phosphite completely decolorized the reaction mixture. The resulting solution was stirred at room temperature for two days, then was extracted with water, dried over magnesium sulfate, concentrated, and chromatographed (silica gel eluted with 1:1 cyclohexane/ethyl acetate) to afford 20.2 g of diphenyl hydroxymethyl phosphonate as a colorless oil.

For $C_{13}H_{13}O_4P(0.2H_2O)$:

|  | C | H |
| --- | --- | --- |
| Calcd: | 58.30; | 5.04. |
| Found: | 58.58; | 4.96. |

A solution of trifluoromethane sulfonic anhydride (3.19 ml, 18.9 mmol) in methylene chloride (10 ml) was added dropwise to a dry ice/acetone cooled, mechanically stirred solution of 2,6-di-tert-butyl-4-methylpyridine (4.28 g, 20.8 mmol) in methylene chloride (20 ml). The resulting slurry was warmed to −30° C. to effect solution, then was cooled to −78° C. while a solution of diphenyl hydroxymethylphosphonate (5.0 g, 18.9 mmol) in methylene chloride (10 ml) was added dropwise. This reaction mixture was slowly warmed to 0° C., affording a thick, white slurry which was filtered to remove the insoluble 2,6-di-tert-butyl-4-methylpyridinium triflate. The filtrate was diluted with methylene chloride and extracted with saturated aqueous sodium bicarbonate (100 ml), then was dried over magnesium sulfate, concentrated under vacuum, and chromatographed (silica gel eluted with 3:17 ethyl acetate/hexane) to afford 3.2 g (43%) of diphenyl (phosphonomethyl)trifluoromethyl sulfonate as a white solid (mp 71° C.–73° C.).

For $C_{14}H_{12}F_3O_6PS$:

|  | C | H | S |
| --- | --- | --- | --- |
| Calcd. | 42.43; | 3.05; | 8.09 |
| Found: | 42.72; | 3.06; | 7.96. |

EXAMPLE 4

Preparation of Aminomethylphosphonic Acid

A solution of the diethyl(phosphonomethyl)trifluoromethyl sulfonate from Example 1 (3.0 g, 10 mmol) in ethanol (7 ml) was added dropwise to an ice-water cooled solution of concentrated ammonium hydroxide (25 g, 200 mmol) in ethanol (25 ml). Immediately after addition the reaction was complete as evidenced by $^{31}$P-NMR The solvent was removed under vacuum and the residue refluxed in 48% hydrobromic acid (30 ml) for 24 hours. This solution was concentrated to an oil under vacuum, dissolved in ethanol (40 ml), and cooled with an ice-water bath while excess propylene oxide was added dropwise. Aminomethylphosphonic acid (0.77 g, 70%) crystallized as a white solid.

For $CH_6NO_3P$:

|  | C | H | N |
| --- | --- | --- | --- |
| Calcd: | 10.82; | 5.45; | 12.61. |
| Found: | 10.43; | 5.32; | 12.32. |

EXAMPLE 5

Preparation of N-phosphonomethylglycine

A solution of sodium hydroxide (3.67 g, 91.8 mmol) in water (26 ml) was added dropwise to an ice-water cooled solution of glycine (5.22 g, 69.5 mmol) in water (31 ml). Diethyl(phosphonomethyl)trifluoromethyl sulfonate (6.9 g, 23 mmol) from Example 1 was then added in a single portion, and the resulting two-phase mixture was vigorously stirred at 0° C. Within 15 minutes a homogeneous solution formed which was concentrated under vacuum, then was refluxed in 48% hydrobromic acid (75 ml) for 20 hours. This solution was concentrated to a solid, dissolved in a minimum volume of 48% hydrobromic acid, diluted with a large volume of ethanol, cooled to 0° C., and crystallized by the dropwise addition of excess propylene oxide. The N-phosphonomethylglycine was insoluble in the ethanol and crystallized immediately, while glycine crystallized slowly. After three successive fractional crystallizations, 2.9 g (75%) of pure N-phosphonomethylglycine was obtained as a white solid.

EXAMPLE 6

Other (phosphonomethyl)perfluoroalkyl Sulfonates

Using the general method of Examples 1 through 3, the compounds of the present invention that have been prepared include dimethyl(phosphonomethyl)perfluoroalkyl sulfonate, diisopropyl(phosphonomethyl)perfluoroalkyl sulfonate, di-n-octyl(phosphonomethyl)perfluoroalkyl sulfonate, bis(2-cyanoethyl)(phosphonomethyl)perfluoroalkyl sulfonate, dibenzyl(phosphonomethyl)perfluoroalkyl sulfonate, and diethyl(phosphonomethyl)perfluorooctyl sulfonate.

Although the invention has been described in terms of specified embodiments which are set forth in considerable detail, it should be understood that this is by way of illustration only, and that alternative embodiments and operating techniques will become apparent to those skilled in the art in view of the disclosure. For example, other groups can be substituted into the general formula of the compounds of this invention and the resulting product can undergo displacement reactions with various nucleophiles containing sulfur, oxygen, phosphorous, carbon and the like to produce different products than those disclosed herein. Accordingly, modifications can be made without departing from the spirit of the described invention.

What is claimed is:

1. A (phosphonomethyl)perfluoroalkyl sulfonate represented by the formula

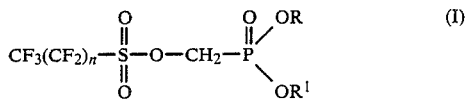

wherein n is from 0 to 7 and R and $R^1$ are independently selected from the group consisting of hydrogen, 2-cyanoethyl, monovalent hydrocarbons containing from 1 to 18 carbons, monovalent hydrocarbonoxyhydrocarbons containing from 1 to 18 carbons, halogenated monovalent hydrocarbons containing from 1 to 18 carbons and from 1 to 3 halogens, halogenated monovalent hydrocarbonoxyhydrocarbons containing from 1 to 18 carbons and from 1 to 3 halogens.

2. A compound of claim 1 wherein R and $R^1$ are independently selected from the group consisting of hydrogen, 2-cyanoethyl and monovalent hydrocarbons.

3. A compound of claim 2 wherein R and $R^1$ are independently selected from monovalent hydrocarbon groups containing 1 to 8 carbons.

4. A compound of claim 3 wherein n is 0.

5. A compound of claim 4 wherein R and $R^1$ are selected from the group consisting of methyl, ethyl, isopropyl, tertiary butyl, phenyl, benzyl, and n-octyl.

6. A compound of claim 2 wherein R and $R^1$ are hydrogen.

7. A compound of claim 6 wherein n is 0.

8. A compound of claim 2 wherein R and $R^1$ are 2-cyanoethyl and n is 0.

* * * * *